(12) United States Patent
Crawford

(10) Patent No.: US 11,596,610 B2
(45) Date of Patent: Mar. 7, 2023

(54) COMPOSITIONS IN SUPPORT OF HEALTH AND MENTAL ACCUITY

(71) Applicant: Sovereignty, Austin, TX (US)

(72) Inventor: Jason Crawford, Austin, TX (US)

(73) Assignee: HIGHER OPTIONS GLOBAL, INC., Austin, TX (US)

( * ) Notice: Subject to any disclaimer, the term of this patent is extended or adjusted under 35 U.S.C. 154(b) by 28 days.

(21) Appl. No.: 17/199,903

(22) Filed: Mar. 12, 2021

(65) Prior Publication Data

US 2021/0283070 A1    Sep. 16, 2021

Related U.S. Application Data

(60) Provisional application No. 62/988,910, filed on Mar. 12, 2020.

(51) Int. Cl.

| | |
|---|---|
| *A61K 31/05* | (2006.01) |
| *A61K 45/06* | (2006.01) |
| *A61K 36/68* | (2006.01) |
| *A61K 36/185* | (2006.01) |
| *A61K 36/82* | (2006.01) |
| *A61K 36/74* | (2006.01) |
| *A61K 36/736* | (2006.01) |
| *A61K 36/45* | (2006.01) |
| *A61K 36/31* | (2006.01) |
| *A61K 36/9066* | (2006.01) |
| *A61K 31/522* | (2006.01) |
| *A61K 36/79* | (2006.01) |
| *A61K 31/4045* | (2006.01) |
| *A61K 31/198* | (2006.01) |
| *A61K 36/21* | (2006.01) |
| *A61K 31/197* | (2006.01) |
| *A61K 36/53* | (2006.01) |
| *A61K 36/81* | (2006.01) |

(52) U.S. Cl.
CPC ............ *A61K 31/05* (2013.01); *A61K 31/197* (2013.01); *A61K 31/198* (2013.01); *A61K 31/4045* (2013.01); *A61K 31/522* (2013.01); *A61K 36/185* (2013.01); *A61K 36/21* (2013.01); *A61K 36/31* (2013.01); *A61K 36/45* (2013.01); *A61K 36/53* (2013.01); *A61K 36/68* (2013.01); *A61K 36/736* (2013.01); *A61K 36/74* (2013.01); *A61K 36/79* (2013.01); *A61K 36/81* (2013.01); *A61K 36/82* (2013.01); *A61K 36/9066* (2013.01); *A61K 45/06* (2013.01)

(58) Field of Classification Search
CPC .... A61K 31/05; A61K 31/197; A61K 31/198; A61K 31/4045; A61K 31/522; A61K 36/185; A61K 36/21; A61K 36/31; A61K 36/45; A61K 36/53; A61K 36/68; A61K 36/736; A61K 36/74; A61K 36/79; A61K 36/81; A61K 36/82; A61K 36/9066; A61K 45/06

See application file for complete search history.

(56) References Cited

U.S. PATENT DOCUMENTS

| | | | |
|---|---|---|---|
| 7,361,372 B2 * | 4/2008 | Golz-Berner | A61K 8/9789 424/773 |
| 10,449,143 B2 * | 10/2019 | Kalathil | A61P 17/00 |
| 10,835,570 B2 * | 11/2020 | Buonamici | A23L 33/15 |
| 11,400,129 B2 * | 8/2022 | Engler | A23K 20/121 |
| 2015/0104523 A1 * | 4/2015 | Lockwood | A61K 31/12 424/535 |

OTHER PUBLICATIONS

Lodha G "Formulation and Evaluation of Polyherbal Shampoo to Promote Hair Growth and Provide Antidandruff Action" J. Drug Delivery and Therapeutics, 2019 (ePub Aug. 30, 2019),9(4-A),pp. 296-300; doi:10.22270/jddt.v9i4-a.3474. (Year: 2019).*

* cited by examiner

*Primary Examiner* — Aaron J Kosar

(57) ABSTRACT

A composition includes a cannabinoid agent in a range of 0.005% to 1%, a terpene agent in a range of 0.005% to 1%, and a co-fermented herbal complex in a range of 5% to 40%. The cannabinoid agent can include CBD, CBN, CBG, or a combination thereof. The composition can further include ashwagandha.

20 Claims, 1 Drawing Sheet

COMPOSITIONS IN SUPPORT OF HEALTH AND MENTAL ACCUITY

CROSS-REFERENCE TO RELATED APPLICATION(S)

This application claims benefit of U.S. Provisional Application No. 62/988,910, filed Mar. 12, 2020, which is incorporated herein by reference in its entirety.

FIELD OF THE DISCLOSURE

This disclosure, in general, is directed to ingestible compositions in support of health and mental acuity and associated methods.

BACKGROUND

Increasingly, people are reporting feeling tired, stressed, and generally in poor health. Modern stressors from the American diet to constant interaction with electronic devices to reduced sleep quality contributed to an increasing occurrence of various chronic ailments and a general feeling of malaise. In particular, operating in high stress environments with constant bombardment with information has contributed the occurrence of ailments associated with adrenal overload.

Further, such conditions reduce sleep quality and busy lifestyles have reduced the amount of sleep many receive each night. Sleep is a time when purportedly, the brain clears waste and undergoes growth. In addition, other parts of the body, such as muscles and various organs, undergo waste removal, growth, and repairs during sleep. With both the reduced time sleeping and the poor quality of sleep, people are reporting lower productivity and less enjoyment of life. Thus, work suffers, relationships suffer, and chronic ailments arise in the absence of consistent sleep.

As such, the stressors felt during periods of activity and the lack of quality sleep, purportedly, contributed to health issues and a general decrease in mental acuity. As such, compositions that address or improve the quality of sleep or compositions that support productivity without introducing additional stress would be desirable.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

Figure 1:
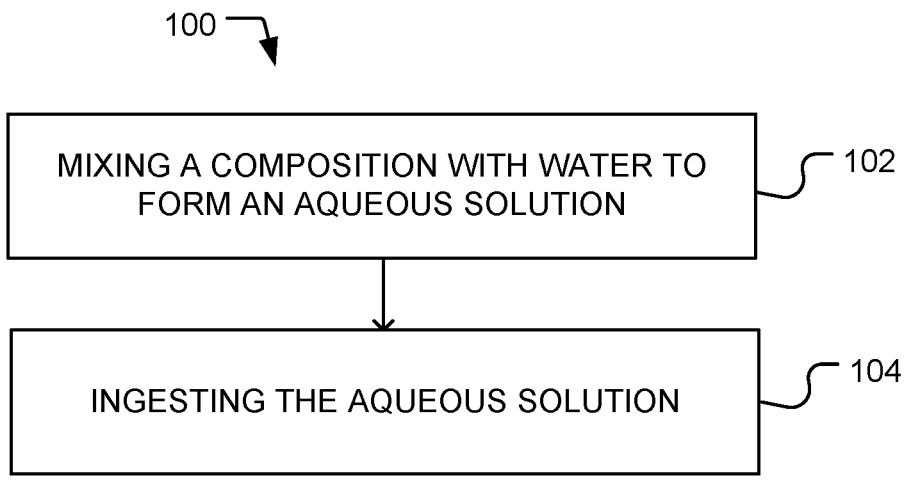
FIG. 1 includes a block flow diagram of an example method of using a composition.

In an embodiment, a composition includes ashwagandha in a range of 5% to 20%, *Bacopa monnieri* in a range of 1% to 10%, and amla in a range of 0.5% to 10%. The composition can further include one or more cannabinoid agents, such as cannabidiol (CBD), cannabinol (CBN) or cannabigerol (CBG). The composition provides benefits in both formulas for improved mental acuity, referred to herein as an alert formula or composition, and formulas for improved sleep, referred to herein as a sleep formula or composition.

In another embodiment, the composition includes a cannabinoid agent, such as cannabinol (CBN) or cannabigerol (CBG). In an example, the composition further includes a co-fermented herbal complex in which a set of herbs are fermented together in the same solution. Optionally, the composition includes a variety of terpenes. In another example, the composition includes ashwagandha. The composition may be in the form of a powder. For example, the power can be mixed with water to form an aqueous solution that is imbibed by a user. Such compositions have use to improve both awake time mental acuity and quality of sleep.

As used herein, percentages are expressed as a weight percent, and weights are expressed on a per dose basis. For example, if a recommended dose of the dry powder composition is 10 grams, the weights of the ingredients of the composition are expressed as weights of the ingredient within 10 grams of the dry powder composition. The compositions can be mixed with water or other liquids and the weights or weight percentages are expressed to not include the water or other liquid because more or less liquid can be used to concentrate or dilute a liquid version of the composition or formula, if any.

The expression per-dose refers to the recommended dose provided with a product including the composition or formula and includes any dose option within the full range of dose options provided with the product. For example, if the product recommends one to two scoops as a dose, the per-dose composition includes the composition of one scoop or the composition of two scoops.

In an example, a composition includes ashwagandha in a range of 5% to 20%, *Bacopa monnieri* in a range of 1% to 10%, and amla in a range of 0.5% to 10%. The composition provides benefits in both formulas for improved mental acuity, referred to herein as an alert formula or composition, and formulas for improved sleep, referred to herein as a sleep formula or composition.

In a particular example, the composition can include the ashwagandha in a range of 7% to 15%. For example, the composition can include the ashwagandha in a range of 9% to 13%. The ashwagandha can include withanolides. For example, the composition can include withanolides in a per dose basis in a range of 5 mg to 30 mg, such as 10 mg to 20 mg.

In another example, the composition can include the *Bacopa monnieri* in a range of 4% to 10%. For example, the *Bacopa monnieri* in a range of 4% to 7%. In an example, the *Bacopa monnieri* includes bacopasides. In particular, the bacopasides can be included in a per dose basis in a range of 50 mg to 300 mg, such as 100 mg to 200 mg.

In an additional example, the composition can include the amla (*Emblica officinalis*) in a range of 1.5% to 5%. The amla can include beta-glucogallin. For example, the composition can include the beta-glucogallin on a per dose bases in a range of 1 mg to 30 mg, such as a range of 3 mg to 10 mg.

In a further example, the composition can include a cannabinoid agent. For example, the composition can include cannabidiol (CBD) in a range of 1% to 10%. In an example, the cannabidiol can be included in a range of 3% to 7%. In another example, the composition includes cannabinol (CBN) in a range of 0.1% to 4%. For example, the cannabinol can be present in a range of 1% to 3%.

The composition finds particular use in either a formula or composition that enhances mental acuity (referred to herein as an alert formula or composition) or a formula or composition that improves sleep (referred to herein as a sleep formula or composition).

In an additional example, an alert composition includes plant-based nitric oxide-inducing ingredients in a range of 0.5% to 10%. For example, the composition includes the plant-based nitric oxide-inducing ingredients are present in a range of 0.5% to 5%, such as in a range of 0.5% to 3%. In a particular example, the plant-based nitric oxide inducing ingredients can include one or more of green coffee bean extract, green tea extract, tart cherry, blueberry, broccoli, kale, or turmeric extract. For example, the pant-based nitric oxide inducing ingredients is a combination of green coffee bean extract, green tea extract, tart cherry, blueberry, broccoli, kale, and turmeric extract, for example, as sold under the trademark/tradename S7™ of FutureCeuticals.

In another example, the alert composition includes coffee fruit extract in a range of 0.5% to 10%. For example, the coffee fruit extract is present in a range of 0.5% to 5%. In another example, the coffee fruit extract is present in a range of 0.5% to 3%.

In a further example, the alert composition includes grape seed extract in a range of 1% to 10%. For example, the grape seed extract is present in a range of 1% to 5%. In particular, the grape seed extract can include proanthocyanidins. For example, the alert composition can include 25 mg to 200 mg of the proanthocyanidins, such as 50 mg to 120 mg of the proanthocyanidins.

In an additional example, the alert composition includes *Cordyceps* (*Cordyceps sinensis*) in a range of 5% to 20%. For example, the alert composition can include the *Cordyceps* in a range of 7% to 15%, such as a range of 9% to 13%. The *Cordyceps* can include cordycepic acid. The alert composition can include the cordycepic acid in an amount in a range of 5 mg to 50 mg, such as a range of 10 mg to 30 mg.

In another example, the alert composition includes extended-release caffeine in a range of 0.5% to 10%. For example, the extended-release caffeine can be included in a range of 0.5% to 5%, such as a range of 0.5% to 3%. In particular, the various coffee products and extracts and the extended-release caffeine provide caffeine to the alert composition. For example, the alert composition can include 50 mg to 500 mg caffeine, such as 50 mg to 350 mg, or 100 mg to 250 mg caffeine on a per dose basis, in both or either quick release or extended-release variations.

In a further example, the alert composition includes whole coffee fruit extract in a range of 1% to 10%. For example, the whole coffee fruit extract is present in a range of 1% to 5%.

In an additional example, the alert composition includes *Schisandra* extract in a range of 1% to 10%. For example, the *Schisandra* extract is present in a range of 4% to 10%, such as in a range of 4% to 7%.

In another example, the alert composition includes L-theanine in a range of 1% to 10%. For example, the L-theanine is present in a range of 4% to 10%, such as in a range of 4% to 7%.

In an additional example, the alert composition includes beet juice in dried form in a range of 20% to 60%. For example, the beet juice is present in a range of 30% to 50%.

The alert composition can further include dextrin and various flavorings.

In an example, the composition can be used along with other ingredients to form a sleep composition. For the example, the sleep composition can include melatonin in a range of 0.005% to 1%. The melatonin can be included in a range of 0.01% to 0.5%, such as in a range of 0.01% to 0.1%.

In another example, the sleep composition can include Bluenesse (*Melissa officinalis* leaf extract) in a range of 3% to 20%. For example, the *Melissa officinalis* leaf extract is present in a range of 5% to 18%, such as in a range of 10% to 15%.

In a further example, the sleep composition can include holy basil (*Ocimum tenuiflorum*) in a range of 20% to 60%. For example, the holy basil is present in a range of 30% to 50%.

In another example, the sleep composition can include gamma aminobutyric acid in a range of 0.5% to 10%. For example, the gamma aminobutyric acid is present in a range of 1.5% to 5%.

In another example, the sleep composition includes L-theanine in a range of 1% to 10%. For example, the L-theanine is present in a range of 4% to 10%, such as in a range of 6% to 9%.

In a particular example, an alert composition consists essentially of ashwagandha in a range of 5% to 20%, *Bacopa monnieri* in a range of 1% to 10%, amla in a range of 0.5% to 10%, cannabidiol in a range of 1% to 10%, cannabinol in a range of 0.1% to 4%, plant-based nitric oxide-inducing ingredients in a range of 0.5% to 10%, coffee fruit extract in a range of 0.5% to 10%, grape seed extract in a range of 1% to 10%, *Cordyceps* in a range of 5% to 20%, extended-release caffeine in a range of 0.5% to 10%, whole coffee fruit extract in a range of 1% to 10%, *Schisandra* extract in a range of 1% to 10%, L-theanine in a range of 1% to 10%, beet juice in a range of 20% to 60%, and dextrin.

In an example, the plant-based nitric oxide inducing ingredients include one or more of green coffee bean extract, green tea extract, tart cherry, blueberry, broccoli, kale, or turmeric extract.

In a particular example, a sleep composition consists essentially of ashwagandha in a range of 5% to 20%, *Bacopa monnieri* in a range of 1% to 10%, amla in a range of 0.5% to 10%, cannabidiol in a range of 1% to 10%, cannabinol in a range of 0.1% to 4%, melatonin in a range of 0.005% to 1%, *Melissa officinalis* leaf extract in a range of 3% to 20%, holy basil (*Ocimum tenuiflorum*) in a range of 20% to 60%, and gamma aminobutyric acid in a range of 0.5% to 10%. The sleep composition can further include sweeteners and flavorings.

In a further example, an alternative alert composition consists essentially of complex terpenes in a range of 0.5% to 10%, coffee fruit extract in a range of 5% to 20%, organic coffeeberry in a range of 5% to 20%, plant-based nitric oxide-inducing ingredients in a range of 0.5% to 10%, cannabidiol in a range of 0.1% to 5%, cannabinol in a range of 0.1% to 3%, epigallocatechin gallate in a range of 0.005% to 1%, and resveratrol in a range of 0.005% to 1%. The composition can further include sweeteners, such as dextrin and monk fruit extract, and flavorings, such as citric acid.

In an example, the complex terpenes are present in a range of 0.5% to 5%, such as in a range of 0.5% to 3%. For example, the complex terpenes can include alpha pinene, limonene, beta caryophyllene, phytol, alpha phellandrene, alpha-humulene, nerolidol, myrcene, linalool, terpinolene, or any combination thereof.

In another example, the coffee fruit extract is present in a range of 10% to 15%. In a further example, the organic coffeeberry is present in a range of 10% to 15%.

In an additional example, the plant-based nitric oxide-inducing ingredients are in a range of 1% to 10%, such as in a range of 2% to 8%.

In a further example, the cannabidiol is present in a range of 0.5% to 3%. In an additional example, the cannabinol is present in a range of 0.5% to 2%.

In another example, the epigallocatechin gallate is present in a range of 0.01% to 0.5%. For example, the epigallocatechin gallate is present in a range of 0.01% to 0.1%.

In a further example, the resveratrol is present in a range of 0.01% to 0.5%. For example, the resveratrol is present in a range of 0.01% to 0.1%.

In another alternative example, the composition includes a cannabinoid agent, a terpene agent, and co-fermented herbal complex. For example, the composition may be a dry powdered mixture. In another example, the composition can be in the form of an aqueous solution.

The cannabinoid agent can include CBD (cannabidiol), CBDA (cannabidiolic acid), CBN (cannabinol), CBG (cannabigerol), CBC (cannabichromene), CBL (cannabicyclol), CBV (cannabivarin), THCV (tetrahydrocannabivarin), CBDV (cannabidivarin), CBCV (cannabichromevarin), CBGV (cannabigerovarin), CBGM (cannabigerol monomethyl ether), CBE (cannabielsoin), CBT (cannabicitran), or any combination thereof. In general, the cannabinoid agent is free of THC (tetrahydrocannabinol) or THCA (tetrahydrocannabinolic acid). In particular, the cannabinoid includes CBD, CBN, CBG, or combination thereof. In example, the cannabinoid agent includes CBG. In another example, the cannabinoid agent includes CBN. The cannabinoid agent can be included in the composition in a range of 0.005% to 1%. For example, the cannabinoid agent can be included in the composition in a range of 0.01% to 1%, such as a range of 0.01% to 0.5%.

The terpene agent can include limonene, alpha pinene, beta pinene, camphene, mycene, eucalyptol, terpinolene, alpha bislol, beta caryophyllene, humulene, linalool, nerolidol, ocimene, or a combination thereof. In an example, the terpene agent includes a mixture including limonene, alpha pinene, beta pinene, camphene, mycene, eucalyptol, terpinolene, or a combination thereof. In another example, the terpene agent includes camphene, mycene, terpinolene, alpha bislol, beta caryophyllene, humulene, linalool, nerolidol, ocimene, or a combination thereof. The terpene agent can be included in the composition in a range of 0.005% to 1%. For example, the terpene agent can be included in the composition in a range of 0.1% to 0.5%.

Regarding the co-fermented herbal complex, each of the ingredients can be fermented together and subsequently dried to form a powder complex having synergistic properties. In an example, the co-fermented herbal complex can include ginseng, maidenhair tree (*Ginkgo biloba*), Mongolian milkvetch (*Astragalus membranaceus*), magnolia vine (*Schisandra chinensis*), fo-ti (*Polygonum multiflorum*), hardy rubber Tree (*Eucommiae ulmoides*), Solomon's seal (*Polygonatum sibirica*), hijiki seaweed (*Sargassum fusiforme*), white *Atractylodes* (*Atractylodes macrocephala*), reishi mushroom (*Ganoderma lucidum*), or any combination thereof. The ginseng of the co-fermented herbal complex can include Siberian ginseng (*Eletherococcus senticosus*), Chinese ginseng (*Panax ginseng*), southern ginseng (*Gynostemma pentaphylla*), or any combination thereof. The co-fermented herbal complex can further include jujube fruit (*Ziziphus jujuba*), Goji berry (*Lycium barbarum*), monk fruit (*Momordica grosvenori*), or any combination thereof. In another example, the for co-fermented herbal complex includes Siberian ginseng (*Eletherococcus senticosus*), maidenhair tree (*Ginkgo biloba*), Mongolian milkvetch (*Astragalus membranaceus*), Chinese ginseng (*Panax ginseng*), magnolia vine (*Schisandra chinensis*), fo-ti (*Polygonum multiflorum*), hardy rubber Tree (*Eucommiae ulmoides*), Solomon's seal (*Polygonatum sibirica*), southern ginseng (*Gynostemma pentaphylla*), hijiki seaweed (*Sargassum fusiforme*), white *Atractylodes* (*Atractylodes macrocephala*), reishi mushroom (*Ganoderma lucidum*), jujube fruit (*Ziziphus jujuba*), Goji berry (*Lycium barbarum*), monk fruit (*Momordica grosvenori*), or any combination thereof. In a further example, the co-fermented herbal complex includes Chinese jujube seed (*Ziziphus jujuba*), Chinese thoroughwax (*Bupleurum falcatum*), Chinese senega root (*Poygala tenuifolia*), *Albizia* bark (*Albizzia julibrissin*), *Sophora* root (*Sophora flavescens*), or any combination thereof.

The co-fermented herbal complex can be included in the composition in a range of 5% to 40%. For example, the co-fermented herbal complex is included in the composition in a range of 10% to 30%, such as a range of 15% to 35%.

The composition can further include fermented beet. For example, the fermented beet can be fermented beet crystals. The fermented beet can be included in the composition in the range of 1% to 30%, such as a range of 5% to 20%.

In addition, the composition can include *Rhodiola rosea*. The *Rhodiola rosea* can be a fermented *Rhodiola rosea*. In an example, the *Rhodiola rosea* is included in the composition in a range of 1% to 10%, such as a range of 2% to 7%.

The composition can further include *Cordyceps sinensis*. The *Cordyceps sinensis* can include fermented *Cordyceps sinensis*. In the example, the *Cordyceps sinensis* is included in the composition in a range of 1% to 10%, such as a range of 2% to 7%.

In a further example, the composition can include hemp extract, such as THC-free hemp extract. The hemp extract can be included in the composition in a range of 0.01% to 2%, such as a range of 0.05% to 1%.

In an additional example, the composition can include *Bacopa monnieri*. The *Bacopa monnieri* can be included in the composition in a range of 1% to 10%. For example, the *Bacopa monnieri* can be included in a range of 2% to 7%.

The composition can also include L-theanine, such as fermented L-theanine. In an example, the L-theanine is included in the composition in a range of 1% to 10%, such as a range of 1% to 6%.

In another example, the composition can include whole bean coffee fruit powder. For example, the whole bean coffee fruit powder can be included in the composition in a range of 0.1% to 5%. For example, the whole bean coffee fruit powder can be included in the composition in a range of 0.5% to 3%.

The composition can also include caffeine, such as an organic derived caffeine. The caffeine can be included in the composition in a range of 0.5% to 10%, such as a range of 1% to 5%.

The composition can also include a nitric oxide booster. In an example, the nitric oxide booster includes coffee bean extract, green tea extract, turmeric extract, tart cherry, blueberry, broccoli, kale, or any combination thereof. The nitric oxide booster can be included in the composition in a range of 0.01% to 5%, such as a range of 0.1% to 2%.

In another example, the composition can include astaxanthin. For example, the composition can include astaxanthin in a range of 0.01% to 2%, such as a range of 0.01% to 1%.

In an additional example, the composition can include xanthohumol. For example, the composition can include the xanthohumol in a range of 0.01% to 2%, such as a range of 0.01% to 1%.

In a further example, the composition can include a source of magnesium, such as magnesium oxide or magnesium salt. The magnesium salt can include magnesium chloride, magnesium nitrate, or an organic magnesium salt. In particular, the magnesium salt can be an organic magnesium salt, such as magnesium citrate, magnesium glycinate, magnesium ascorbate, or any combination thereof. The magnesium salt can be included in the composition in the range of 1% to 15%, such as a range of 2% to 10%.

In another example, the composition can include ashwagandha, such as an organic ashwagandha. For example, the ashwagandha can be included in the composition in a range of 1% to 15%, such as a range of 2% to 10%.

In a further example, the composition can include valerian root. For example, the valerian root can be included in the composition in a range of 0.1% to 2%, such as a range of 0.1% to 1%.

In a further example, the composition can include melatonin. The melatonin can be included in a composition in a range of 0.005% to 0.5%, such as a range of 0.01% to 0.1%.

The composition can further include flavoring, such as fruit flavoring or extracts; sweeteners, such as sugar or stevia; salts, such as sodium chloride or potassium chloride; citric acid; or any combination thereof. The composition can also include fillers, such as starch, maltodextrin, sodium carbonate, sodium bicarbonate, calcium carbonate, or any combination thereof. In a particular example, the filler includes maltodextrin. In a further example, the composition can include a dispersant, such as lecithin.

The composition can be in a powder form. Alternatively, the composition can be in the form of pressed tablets or in the form of capsules. In a further example, the composition can be mixed with water to form an aqueous solution.

In a particular example, an awake composition can promote mental acuity during periods when users are awake. For example, the composition can include a cannabinoid agent, such as CBG, a terpene agent, and a co-fermented herbal complex. Optionally, the awake composition can include *Rhodiola rosea, Cordyceps sinensis*, or astaxanthin, or any combination thereof.

In an example, the awake composition includes the cannabinoid agent in a range of 0.05% to 1%. For example, the cannabinoid agent can be included in the awake composition in a range of 0.01% to 1%, such as a range of 0.1% to 0.5%. On a per dose basis, the cannabinoid agent can be included in the awake composition in a range of 0.5 mg to 5 mg. For example, the cannabinoid agent can be included in the awake composition in a range of 0.5 mg to 3 mg, such as a range of 1 mg to 2.5 mg.

The terpene agent can include limonene, alpha pinene, beta pinene, camphene, mycene, eucalyptol, terpinolene, alpha bislol, beta caryophyllene, humulene, linalool, nerolidol, ocimene, or a combination thereof. For example, the terpene agent can include limonene, alpha pinene, beta pinene, camphene, mycene, eucalyptol, terpinolene, or a combination thereof. In an example, the terpene agent is included in the awake composition in a range of 0.05% to 1%. For example, the terpene agent can be included in the awake composition in a range of 0.005% to 1%, such as a range of 0.1% to 0.5%. On a per dose basis, the terpene agent can be included in the awake composition in a range of 1 mg to 10 mg. For example, the terpene agent can be included in the awake composition in a range of 2 mg to 7 mg.

The co-fermented herbal complex can include ginseng, maidenhair tree (*Ginkgo biloba*), Mongolian milkvetch (*Astragalus membranaceus*), magnolia vine (*Schisandra chinensis*), fo-ti (*Polygonum multiflorum*), hardy rubber Tree (*Eucommiae ulmoides*), Solomon's seal (*Polygonatum sibirica*), hijiki seaweed (*Sargassum fusiforme*), white Atractylodes (*Atractylodes macrocephala*), reishi mushroom (*Ganoderma lucidum*), or any combination thereof. The *ginseng* of the co-fermented herbal complex can include Siberian *ginseng* (*Eletherococcus senticosus*), Chinese *ginseng* (*Panax ginseng*), southern *ginseng* (*Gynostemma pentaphylla*), or any combination thereof. The co-fermented herbal complex can further include jujube fruit (*Ziziphus jujuba*), Goji berry (*Lycium barbarum*), monk fruit (*Momordica grosvenori*), or any combination thereof.

The co-fermented herbal complex can be included in the awake composition in a range of 5% to 40%. For example, the co-fermented herbal complex can be included in the awake composition in a range of 10% to 30%, such as a range of 15% to 25%. On a per dose basis, the co-fermented herbal complex can be included in the awake composition in a range of 1500 mg to 3000 mg. For example, the co-fermented herbal complex can be included in the awake composition in a range of 1500 mg to 2500 mg, such as a range of 1750 mg to 2250 mg.

The *Rhodiola rosea* can be a fermented *Rhodiola rosea*. In an example, the *Rhodiola rosea* can be included in the awake composition in a range of 1% to 10%. For example, the *Rhodiola rosea* can be included in the awake composition in a range of 2% to 7%. On a per dose basis, the *Rhodiola rosea* can be included in the awake composition in a range of 200 mg to 500 mg. For example, the *Rhodiola rosea* can be included in the awake composition in a range of 300 mg to 400 mg.

The *Cordyceps sinensis* can be fermented *Cordyceps sinensis*. In an example, the *Cordyceps sinensis* can be included in the awake composition in a range of 1% to 10%. For example, the *Cordyceps sinensis* can be included in the awake composition in a range of 2% to 7%. On a per dose basis, the *Cordyceps sinensis* can be included in the awake composition in a range of 200 mg to 500 mg. For example, the *Cordyceps sinensis* can be included in the awake composition in a range of 300 mg to 400 mg.

The astaxanthin can be included in the awake composition in a range of 0.01% to 2%. For example, the astaxanthin can be included in the awake composition in a range of 0.01% to 1%. On a per dose basis, the astaxanthin can be included in the awake composition in a range of 1 mg to 20 mg, such as a range of 2 mg to 15 mg.

The composition can further include fermented beet, such as fermented beet crystals. In an example, the fermented beet can be included in the awake composition in a range of 1% to 30%, such as a range of 5% to 20%. On a per dose basis, the fermented beet can be included in the awake composition in a range of 600 mg to 1800 mg. For example, the fermented beet can be included in the awake composition in a range of 1000 mg to 1400 mg.

The composition can further include hemp extract, such as THC-free hemp extract. In an example, the hemp extract is included in the awake composition in a range of 0.01% to 2%, such as a range of 0.05% to 1%. On a per dose basis, the hemp extract can be included in the awake composition in a range of 5 mg to 35 mg, such as a range of 10 mg to 25 mg.

The awake composition can further include *Bacopa monnieri*. The *Bacopa monnieri* can be included in the awake composition in a range of 1% to 10%, such as a range of 2% to 7%. On a per dose basis, the *Bacopa monnieri* can be included in the awake composition in a range of 150 mg to 500 mg. For example, the *Bacopa monnieri* can be included in the awake composition in a range of 200 mg to 400 mg.

The awake composition can also include L-theanine, such as a fermented L-theanine. In an example, the L-theanine is included in the awake composition in a range of 1% to 10%, such as a range of 1% to 6%. On a per dose basis, the L-theanine can be included in the awake composition in a range of 100 mg to 400 mg, such as a range of 150 mg to 300 mg.

The awake composition can also include whole coffee being fruit powder. For example, the whole coffee bean fruit powder can be included in the awake composition in a range of 0.1% to 5%, such as a range of 0.5% to 3%. On a per dose basis, the whole coffee bean fruit powder can be included in the awake composition in a range of 10 mg to 300 mg, such as a range of 50 mg to 250 mg.

The awake composition can also include caffeine. For example, the caffeine can be included in the awake composition in a range of 0.5% to 10%, such as a range of 1% to 5%. On a per dose basis, the caffeine is included in the awake composition in a range of 20 mg to 500 mg, such as a range of 100 mg to 400 mg.

The awake composition can further include a nitric oxide booster. In an example, the nitric oxide booster includes coffee bean extract, green tea extract, turmeric extract, tart cherry, blueberry, broccoli, kale, or any combination thereof. The nitric oxide booster can be included in the awake composition in a range of 0.1% to 5%, such as a range of 0.1% to 2%. On a per dose basis, the nitric oxide booster can be included in the awake composition in a range of 10 mg to 150 mg. For example, the nitric oxide booster can be included in the awake composition in a range of 25 mg to 90 mg.

The awake composition can further include flavoring, such as fruit flavoring or extracts; sweeteners, such as sugar, sugar alcohols, or *stevia*; salts, such as sodium chloride or potassium chloride; citric acid; or any combination thereof. The composition can also include fillers, such as starch, maltodextrin, sodium carbonate, sodium bicarbonate, calcium carbonate, or any combination thereof. In a further example, the composition can include a dispersant, such as lecithin.

The awake composition can be in a powder form. Alternatively, the awake composition can be in the form of pressed tablets or in the form of capsules. In a further example, the awake composition can be mixed with water to form an aqueous solution.

In a particular example, the composition can consist essentially of a cannabinoid agent in a range of 0.005% to 1%, the cannabinoid agent including CBG; a terpene agent in a range of 0.005% to 1%; a co-fermented herbal complex in a range of 5% to 40%, wherein the co-fermented herbal complex includes *ginseng*, maidenhair tree (*Ginkgo biloba*), Mongolian milkvetch (*Astragalus membranaceus*), magnolia vine (*Schisandra chinensis*), fo-ti (*Polygonum multiflorum*), hardy rubber Tree (*Eucommiae ulmoides*), Solomon's seal (*Polygonatum sibirica*), hijiki seaweed (*Sargassum fusiforme*), white *Atractylodes* (*Atractylodes macrocephala*), reishi mushroom (*Ganoderma lucidum*), or any combination thereof; fermented beet crystals in a range of 1% to 30%; fermented *Rhodiola rosea* in a range of 1% to 10%; fermented *Cordyceps sinensis* in a range of 1% to 10%; hemp extract in a range of 0.01% to 2%; *Bacopa monnieri* in a range of 1% to 10%; L-theanine in a range of 1% to 10%; whole bean coffee fruit powder in a range of 0.1% to 5%; nitric oxide booster in a range of 0.01% to 5%; caffeine in a range of 0.5% to 10%; and astaxanthin in a range of 0.01% to 2%.

In another example, the composition can consist essentially of, on a per dose basis, a cannabinoid agent in a range of 0.5 mg to 5 mg, the cannabinoid agent including CBG; a terpene agent in a range of 1 mg to 10 mg; a co-fermented herbal complex in a range of 1500 mg to 3000 mg, wherein the co-fermented herbal complex includes *ginseng*, maidenhair tree (*Ginkgo biloba*), Mongolian milkvetch (*Astragalus membranaceus*), magnolia vine (*Schisandra chinensis*), fo-ti (*Polygonum multiflorum*), hardy rubber Tree (*Eucommiae ulmoides*), Solomon's seal (*Polygonatum sibirica*), hijiki seaweed (*Sargassum fusiforme*), white *Atractylodes* (*Atractylodes macrocephala*), reishi mushroom (*Ganoderma lucidum*), or any combination thereof; fermented beet crystals in a range of 600 mg to 1800 mg; fermented *Rhodiola rosea* in a range of 200 mg to 500 mg; fermented *Cordyceps sinensis* in a range of 200 mg to 500 mg; hemp extract in a range of 5 mg to 35 mg; *Bacopa monnieri* in a range of 150 mg to 500 mg; L-theanine in a range of 100 mg to 400 mg; whole bean coffee fruit powder in a range of 10 mg to 300 mg; nitric oxide booster in a range of 10 mg to 150 mg; caffeine in a range of 20 mg to 500 mg; and astaxanthin in a range of 1 mg to 20 mg.

In another example, a composition can support mental acuity through improved sleep. In an example, a sleep supporting composition can include a cannabinoid agent such as CBN, a terpene agent, and ashwagandha.

In an example, the cannabinoid agent, such as CBN, can be included in the sleep supporting composition in a range of 0.005% to 1%. For example, the cannabinoid agent can be included in the sleep supporting composition in a range of 0.01% to 1%, such as a range of 0.01% to 0.5%. On a per dose basis, the cannabinoid agent is included in the sleep supporting composition in a range of 0.5 mg to 5 mg. For example, the cannabinoid agent can be included in the sleep supporting composition in a range of 0.5 mg to 3 mg, such as a range of 1 mg to 2.5 mg.

The terpene agent can include limonene, alpha pinene, beta pinene, camphene, mycene, eucalyptol, terpinolene, alpha bislol, beta caryophyllene, humulene, linalool, nerolidol, ocimene, or a combination thereof. For example, the terpene agent can include camphene, mycene, terpinolene, alpha bislol, beta caryophyllene, humulene, linalool, nerolidol, ocimene, or a combination thereof. In an example, the terpene agent can be included in the sleep supporting composition in a range of 0.005% to 1%, such as a range of 0.005% to 1%, or a range of 0.1% to 5%. On a per dose basis, the terpene agent can be included in the sleep supporting composition in a range of 1 mg to 10 mg, such as a range of 2 mg to 7 mg.

The ashwagandha can be an organic ashwagandha. The ashwagandha can be included in the sleep supporting composition in a range of 1% to 5%. For example, the ashwagandha can be included in the sleep supporting composition in a range of 2% to 10%. On a per dose basis, the ashwagandha can be included in a range of 200 mg to 500 mg, such as a range of 250 mg to 400 mg.

The sleep supporting composition can further include a co-fermented herbal complex. For example, the co-fermented herbal complex can include Chinese jujube seed (*Ziziphus jujuba*), Chinese thoroughwax (*Bupleurum falcatum*), Chinese senega root (*Poygala tenuifolia*), *Albizia* bark (*Albizzia julibrissin*), *Sophora* root (*Sophora flavescens*), or any combination thereof. The co-fermented herbal complex can be included in the sleep supporting composition in a range of 5% to 40%. For example, the co-fermented herbal complex can be included in the sleep supporting composition in a range of 10% to 30%, such as a range of 15% to 25%. On a per dose basis, the co-fermented herbal complex can be included in the sleep supporting composition in a range of 1500 mg to 3000 mg. For example, the co-fermented herbal complex can be included in the sleep supporting composition in a range of 1500 mg to 2500 mg, such as a range of 1750 mg to 2250 mg.

The sleep supporting composition can further include a hemp extract, such as a THC-free hemp extract. For example, the hemp extract can be included in the sleep supporting composition in a range of 0.1% to 2%, such as a range of 0.05% to 1%. On a per dose basis, the hemp extract can be included in the sleep supporting composition in a range of 5 mg to 35 mg. For example, the hemp extract can be included in the sleep supporting composition in a range of 10 mg to 25 mg.

The sleep supporting composition can further include L-theanine, such as a fermented L-theanine. In an example, the L-theanine is included in the sleep supporting composition in a range of 1% to 10%, such as a range of 1% to 6%. On a per dose basis, the L-theanine can be included in the sleep supporting composition in a range of 1 mg to 400 mg, such as a range of 150 mg to 300 mg.

The sleep supporting composition can further include xanthohumol. For example, the xanthohumol can be included in the sleep supporting composition in a range of 0.01% to 2%, such as a range of 0.01% to 1%. On a per dose basis, the xanthohumol can be included in a range of 1 mg to 15 mg, such as a range of 3 mg to 9 mg.

The sleep supporting composition can further include a magnesium source, such as a magnesium oxide or a magnesium salt. In an example, the magnesium salt can include magnesium chloride or an organic magnesium salt. For example, the organic magnesium salt can include magnesium citrate, magnesium glycinate, magnesium ascorbate, or any combination thereof. In a particular example, the magnesium salt includes magnesium glycinate. The magnesium salt can be included in the sleep supporting composition in a range of 1% to 15%, such as a range of 2% to 10%. On a per dose basis, the magnesium salt can be included in the sleep supporting composition in a range of 100 mg to 700 mg, such as a range of 200 mg to 450 mg.

The sleep supporting composition can also include valerian root. For example, the valerian root can be included in the sleep supporting composition in a range of 0.01% to 2%, such as a range of 0.1% to 1%. On a per dose basis, the valerian root can be included in the sleep supporting composition in a range of 5 mg to 50 mg, such as a range of 15 mg to 35 mg.

In addition, the sleep supporting composition can include melatonin. For example, the melatonin can be included in the sleep supporting composition in a range of 0.005% to 0.5%, such as a range of 0.01% to 0.1%. On a per dose basis, the sleep supporting composition can include melatonin in a range of 0.1 mg to 10 mg, such as a range of 0.5 mg to 4 mg.

The sleep supporting composition can be in a powder form. Alternatively, the sleep supporting composition can be in the form of pressed tablets or in the form of capsules. In a further example, the sleep supporting composition can be mixed with water to form an aqueous solution.

In a further example, the sleep supporting composition can include the cannabinoid agent such as CDN, a terpene agent, ashwagandha, melatonin, and a co-fermented herbal complex. For example, the terpene agent can be an agent as described above in relation to the sleep supporting composition. The co-fermented herbal complex can be the co-fermented herbal complex described above in relation to the sleep supporting composition. The sleep supporting composition may include the cannabinoid agent, the terpene agent, ashwagandha, melatonin, and the co-fermented herbal complex in the amounts and ranges described above in relation to the sleep supporting composition.

In a particular example, the sleep supporting composition consists essentially of a cannabinoid agent in a range of 0.005% to 1%, the cannabinoid agent including CBN; a terpene agent in a range of 0.005% to 1%; ashwagandha in a range of 1% to 15%; hemp extract in a range of 0.01% to 2%; L-theanine in a range of 1% to 10%; xanthohumol in a range of 0.01% to 2%; magnesium salt in a range of 1% to 15%; valerian root in a range of 0.01% to 2%; melatonin in a range of 0.005% to 0.5%; and a co-fermented herbal complex in a range of 5% to 40%.

In a further example, the sleep supporting composition consists essentially of, on a per dose basis, a cannabinoid agent in a range of 0.5 mg to 5 mg, the cannabinoid agent including CBN; a terpene agent in a range of 1 mg to 10 mg; ashwagandha in a range of 200 mg to 500 mg; hemp extract in a range of 5 mg to 35 mg; L-theanine in a range of 100 mg to 400 mg; xanthohumol in a range of 1 mg to 15 mg; magnesium salt in a range of 100 mg to 700 mg; valerian root in a range of 5 mg to 50 mg; melatonin in a range of 0.1 mg to 10 mg; and a co-fermented herbal complex in a range of 1500 mg to 3000 mg.

The above compositions can further include flavoring, such as fruit flavoring or extracts; sweeteners, such as sugar, sugar alcohols, or *stevia*; salts, such as sodium chloride or potassium chloride; citric acid; or any combination thereof. The compositions can also include fillers, such as starch, maltodextrin, sodium carbonate, sodium bicarbonate, calcium carbonate, or any combination thereof. In a particular example, the filler includes maltodextrin. In a further example, the compositions can include a dispersant, such as lecithin.

The above compositions, including the alert composition, the sleep composition, the awake composition, and the sleep supporting composition, can be ingested. In an example method 100 illustrated in FIG. 1, the composition can be mixed into water to form an aqueous solution, as illustrated at block 102. For example, the composition can be in a dry powder form having flavor, fillers, and dispersants as part of the composition. A scoop, such as approximately 10 g, can be mixed into a water to form an aqueous solution. The aqueous solution can then be ingested, as illustrated at block 104. For example, a user may drink the aqueous solution.

Alternatively, the compositions can be in pill form, such as capsules or pressed tablets. In such an example, the pills can be ingested, for example, by swallowing.

Figure 2:
FIG. 2 includes a block flow diagram of an example method of making a composition.

The compositions, including the awake composition and the sleep supporting composition, can be formed by mixing powdered dry ingredients. For example, in a method 200 illustrated in FIG. 2, dry powdered ingredients can be mixed to form a dry powder composition, as illustrated at block 202. The dry powdered ingredients can be mixed in quantities consistent with per dose amounts. For example, to make a 100-dose batch, dry powdered ingredients can be added at weights equal to 100 times the per dose amount.

Each of the compositions (the alert composition, the sleep composition, the awake composition, and the sleep supporting composition) have desirable benefits when taken separately and act synergistically when used together. In other words, benefits inure from taking the awake composition without taking the sleep supporting composition, and benefits inure from taking the sleep composition without taking the awake composition. And, additional synergistic benefits are experienced when taking both, one while awake and one near bedtime.

In particular, users taking the alert or awake composition report greater mental acuity during waking hours. Similarly, users report feeling less stress and better mental acuity after taking the sleep supporting composition prior to sleeping. Moreover, users report a synergistic effect of feeling greater mental acuity and lower stress when taking both the alert or awake composition during waking hours and the sleep or sleep supporting composition prior to sleeping.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A composition consisting essentially by weight percent thereof:
   ashwagandha in a range of 5% to 20%;
   *Bacopa monnieri* in a range of 1% to 10%;
   amla in a range of 0.5% to 10%;
   cannabidiol in a range of 1% to 10%;
   cannabinol in a range of 0.1% to 4%;
   plant-based nitric oxide-inducing ingredients in a range of 0.5% to 10%;
   coffee fruit extract in a range of 0.5% to 10%;
   grape seed extract in a range of 1% to 10%;
   *Cordyceps* in a range of 5% to 20%;
   extended-release caffeine in a range of 0.5% to 10%;
   whole coffee fruit extract in a range of 1% to 10%;
   *Schisandra* extract in a range of 1% to 10%;
   L-theanine in a range of 1% to 10%;
   beet juice in a range of 20% to 60%; and
   dextrin.

2. The composition of claim 1, wherein the ashwagandha is present in a range of 9% to 13%.

3. The composition of claim 1, wherein the *Bacopa monnieri* is present in a range of 4% to 10%.

4. The composition of claim 3, wherein the *Bacopa monnieri* is present in a range of 4% to 7%.

5. The composition of claim 1, wherein the amla is present in a range of 1.5% to 5%.

6. The composition of claim 5, wherein the cannabidiol is present in a range of 3% to 7%.

7. The composition of claim 1, wherein the cannabinol is present in a range of 1% to 3%.

8. The composition of claim 1, wherein the plant-based nitric oxide-inducing ingredients are present in a range of 0.5% to 5%.

9. The composition of claim 8, wherein the plant-based nitric oxide-inducing ingredients are present in a range of 0.5% to 3%.

10. The composition of claim 1, wherein the plant-based nitric oxide inducing ingredients include one or more of green coffee bean extract, green tea extract, tart cherry, blueberry, broccoli, kale, or turmeric extract.

11. The composition of claim 1, wherein the coffee fruit extract is present in a range of 0.5% to 5%.

12. The composition of claim 11, wherein the coffee fruit extract is present in a range of 0.5% to 3%.

13. The composition of claim 1, wherein the grape seed extract is present in a range of 1% to 5%.

14. The composition of claim 1, wherein the *Cordyceps* is present in a range of 7% to 15%.

15. The composition of claim 14, wherein the *Cordyceps* is present in a range of 9% to 13%.

16. The composition of claim 1, wherein the extended-release caffeine is present in a range of 0.5% to 5%.

17. The composition of claim 1, wherein the whole coffee fruit extract is present in a range of 1% to 5%.

18. The composition of claim 1, wherein the *Schisandra* extract is present in a range of 4% to 10%.

19. The composition of claim 1, wherein L-theanine is present in a range of 4% to 10%.

20. The composition of claim 1, wherein the beet juice is present in a range of 30% to 50%.

* * * * *